US009486177B2

(12) United States Patent
Kimoto et al.

(10) Patent No.: US 9,486,177 B2
(45) Date of Patent: Nov. 8, 2016

(54) X-RAY COMPUTED TOMOGRAPHY APPARATUS, MEDICAL IMAGE PROCESSING APPARATUS, AND MEDICAL IMAGE PROCESSING METHOD

(71) Applicant: Toshiba Medical Systems Corporation, Otawara-shi (JP)

(72) Inventors: Tatsuya Kimoto, Otawara (JP); Kazumasa Arakita, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/251,250

(22) Filed: Apr. 11, 2014

(65) Prior Publication Data
US 2014/0219416 A1    Aug. 7, 2014

Related U.S. Application Data

(63) Continuation of application No. PCT/JP2012/076503, filed on Oct. 12, 2012.

(30) Foreign Application Priority Data

Oct. 14, 2011  (JP) ................. 2011-227205
Oct. 11, 2012  (JP) ................. 2012-226247

(51) Int. Cl.
*A61B 6/00* (2006.01)
*A61B 6/03* (2006.01)
(Continued)

(52) U.S. Cl.
CPC ............ *A61B 6/5217* (2013.01); *A61B 6/032* (2013.01); *A61B 6/50* (2013.01); *A61B 6/5205* (2013.01);
(Continued)

(58) Field of Classification Search
CPC .. A61B 6/032; G01N 23/046; G01N 23/083; G06F 19/321; G06T 7/0012; G06T 7/0048; G06T 7/0081; G06T 7/0083; G06T 7/0085; G06T 7/0093; G06T 7/0097; G06T 2207/10081; G06T 2207/30061; G06T 2207/30064; G06T 2207/30004
USPC .................... 378/4, 210; 382/128, 131, 132
See application file for complete search history.

(56) References Cited

FOREIGN PATENT DOCUMENTS

CN    1418353 A    5/2003
JP    2003-10171 A    1/2003
(Continued)

OTHER PUBLICATIONS

Chinese Office Action issued Sep. 17, 2014, in China Patent Application No. 201280001682.7 (with English translation).
(Continued)

*Primary Examiner* — Jurie Yun
(74) *Attorney, Agent, or Firm* — Oblon, McClelland, Maier & Neustadt, L.L.P

(57) ABSTRACT

An X-ray computed tomography apparatus includes an X-ray tube, an X-ray detector, a volume data reconstruction unit, a lung field region specifying unit, a discrimination unit, an image generation unit, and a display unit. The volume data reconstruction unit reconstructs first volume data of a chest region of an object based on an output from the X-ray detector. The lung field region specifying unit specifies a lung field region of the object in the first volume data. The discrimination unit generates second volume data in which a low CT value region is discriminated from a region other than the low CT value region in the lung field region. The image generation unit generates an image representing a two-dimensional distribution concerning an existing ratio of the low CT value region to the lung field region based on the second volume data.

19 Claims, 9 Drawing Sheets

(51) Int. Cl.
*G06T 7/00* (2006.01)
*G06T 11/00* (2006.01)

(52) U.S. Cl.
CPC ........... *G06T 7/0081* (2013.01); *G06T 11/003* (2013.01); *G06T 2207/10081* (2013.01); *G06T 2207/20148* (2013.01); *G06T 2207/30061* (2013.01)

(56) References Cited

FOREIGN PATENT DOCUMENTS

| JP | 2004-049498 | * | 2/2004 |
| JP | 2004-49498 A | | 2/2004 |
| JP | 2004-105643 A | | 4/2004 |
| JP | 2005-192656 A | | 7/2005 |
| JP | 2009-45286 A | | 3/2009 |
| WO | 2011/040018 A1 | | 4/2011 |

OTHER PUBLICATIONS

International Search Report issued on Nov. 6, 2012 for PCT/JP2012/076503 filed on Oct. 12, 2012 with English Translation.
International Written Opinion mailed on Nov. 6, 2012 for PCT/JP2012/076503 filed on Oct. 12, 2012.
International Preliminary Report on Patentability and Written Opinion issued on Apr. 24, 2014 in PCT/JP2012/076503 (submitting English translation only).

* cited by examiner

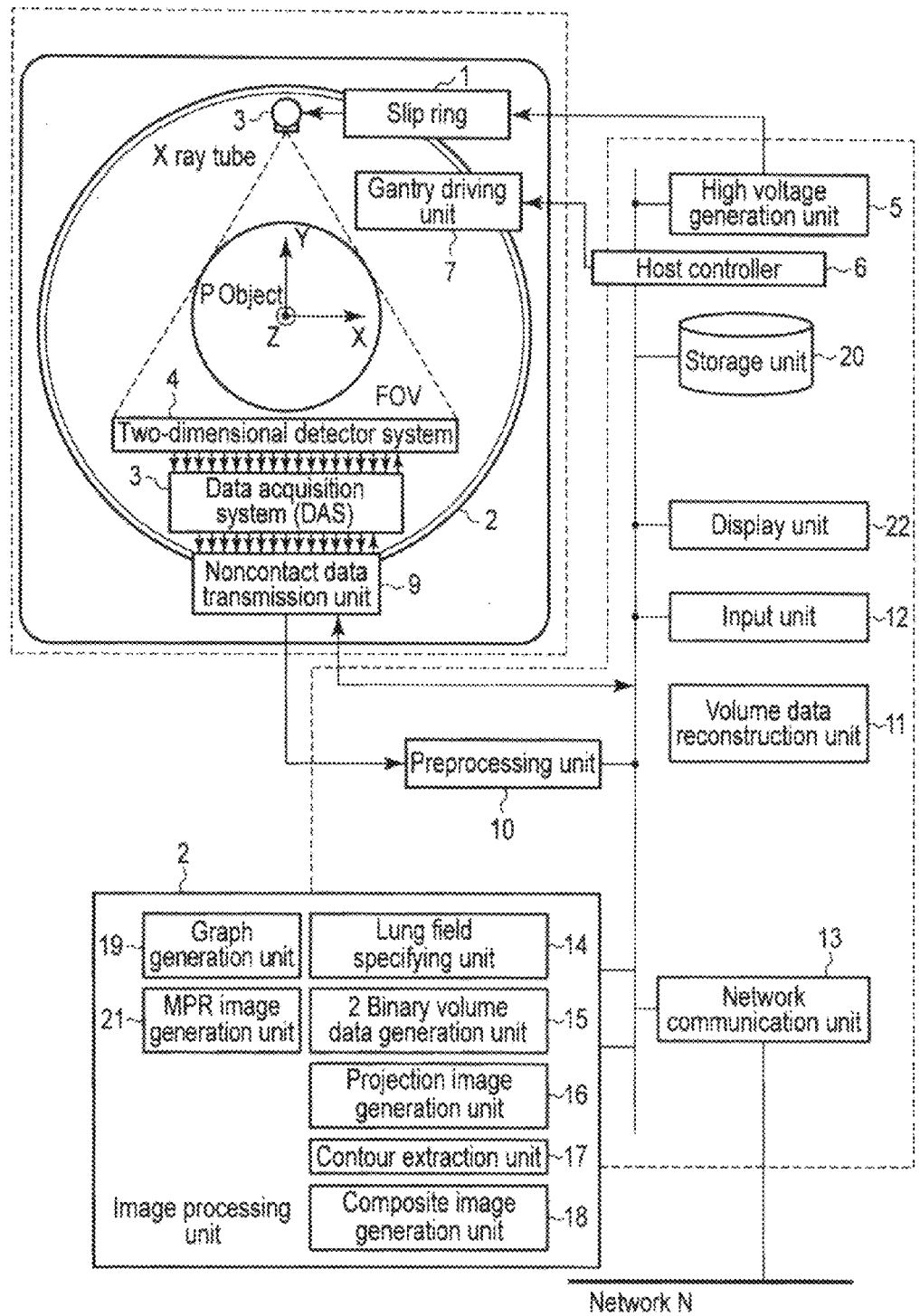
F I G. 1

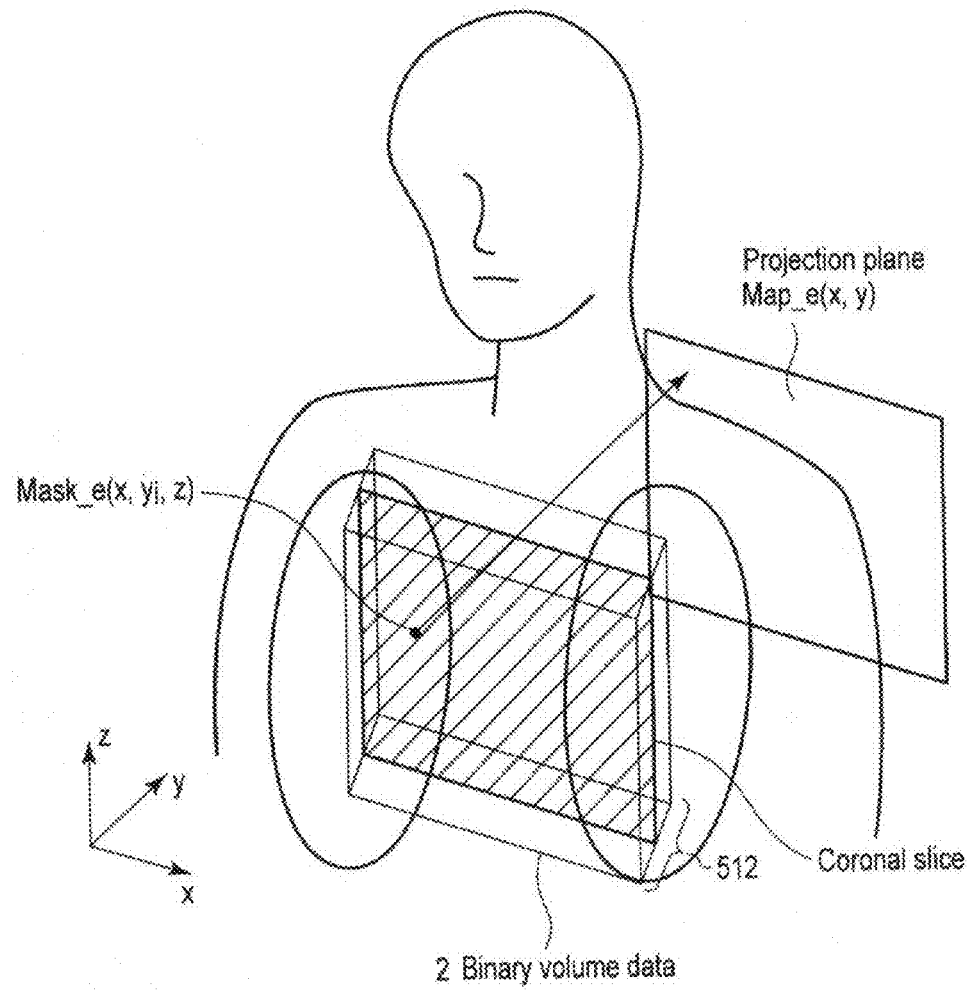
F I G. 11

US 9,486,177 B2

X-RAY COMPUTED TOMOGRAPHY APPARATUS, MEDICAL IMAGE PROCESSING APPARATUS, AND MEDICAL IMAGE PROCESSING METHOD

CROSS-REFERENCE TO RELATED APPLICATION

This application is a Continuation Application of PCT Application No. PCT/JP2012/076503, filed Oct. 12, 2012 and based upon and claims the benefit of priority from Japanese Patent Applications No. 2011-227205, filed Oct. 14, 2011, and No. 2012-226247, filed Oct. 11, 2012, the entire contents of all of which are incorporated herein by reference.

FIELD

Embodiments described herein relate generally to an X-ray computed tomography apparatus, medical image processing apparatus, and medical image processing method.

BACKGROUND

There is available a method of allowing a user to visually grasp the presence/absence of emphysema or an emphysema distribution in the lung field regions by observing the MPR image depicting the lung fields, which are obtained by imaging the chest region of an object using an X-ray computed tomography apparatus. There is also available a method of making an X-ray computed tomography apparatus display low CT value regions in color, which are extracted from the lung fields by performing threshold processing for CT values.

BRIEF DESCRIPTION OF THE DRAWINGS

FIG. 1 is a block diagram showing the internal arrangement of an X-ray computed tomography apparatus according to this embodiment.

FIG. 11 is a schematic view showing a procedure up to the generation of a projection image depicting the distributions of low CT value regions included in volume data from a plurality of coronal slices generated from the volume data by the MPR image generation unit in FIG. 1.

DETAILED DESCRIPTION

Figure 2:
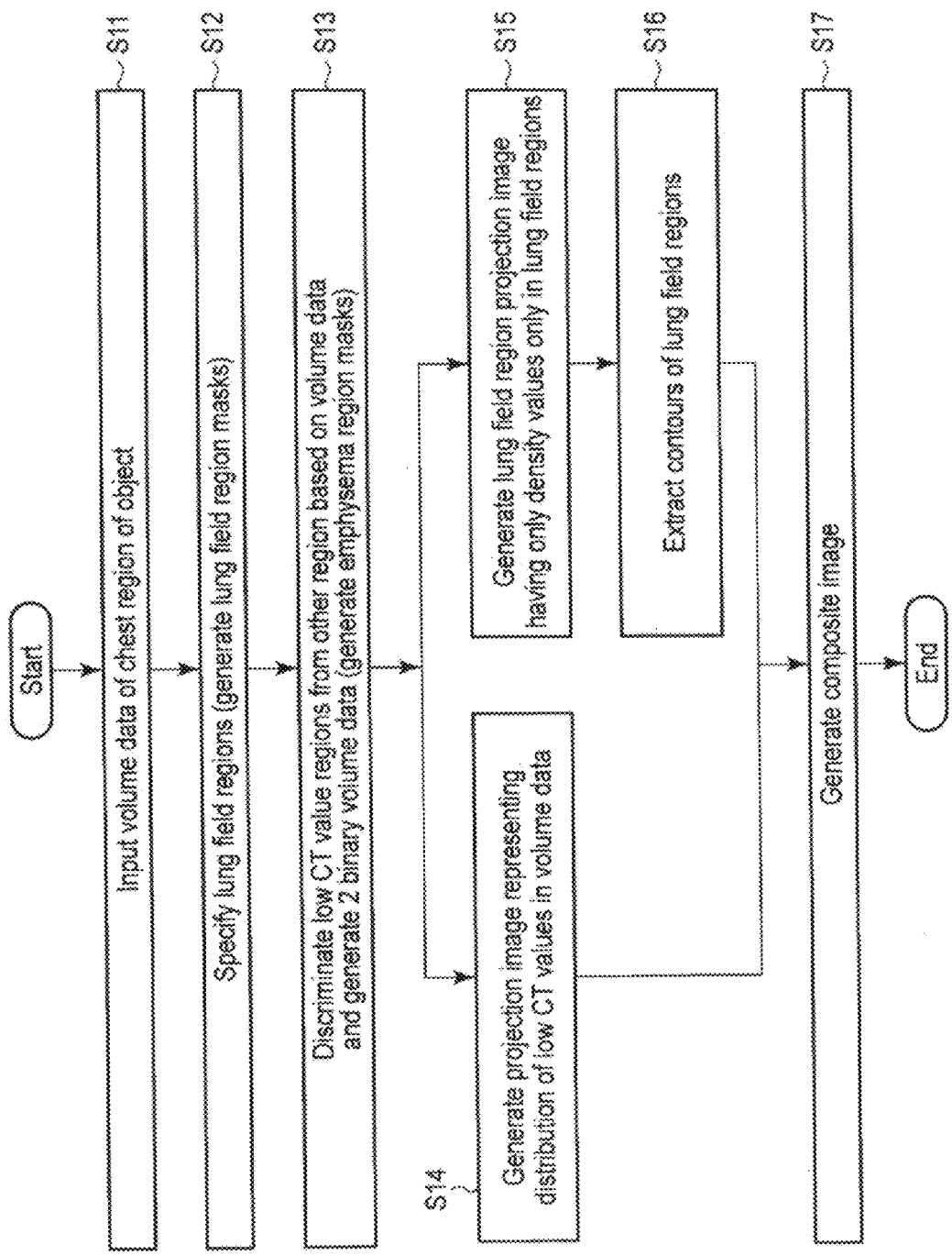
FIG. 2 is a flowchart showing image processing according to this embodiment.

In general, according to one embodiment, an X-ray computed tomography apparatus includes an X-ray tube, an X-ray detector, a volume data reconstruction unit, a lung field region specifying unit, a discrimination unit, an image generation unit, and a display unit. The X-ray tube is configured to generate X-rays. The X-ray detector is configured to detect X-rays generated from the X-ray tube and transmitted through an object. The volume data reconstruction unit is configured to reconstruct first volume data of a chest region of the object based on an output from the X-ray detector. The lung field region specifying unit is configured to specify a lung field region of the object in the first volume data. The discrimination unit is configured to generate second volume data in which a low CT value region is discriminated from a region other than the low CT value region in the lung field region. The image generation unit is configured to generate an image representing a two-dimensional distribution concerning an existing ratio of the low CT value region to the lung field region based on the second volume data. The display unit is configured to display the image representing the two-dimensional distribution.

An embodiment will be described below with reference to the accompanying drawing. Note that the same reference numerals in the following description denote constituent elements having almost the same functions and arrangements, and a repetitive description will be made only when required.

FIG. 1 is a block diagram showing the arrangement of an X-ray computed tomography apparatus according to this embodiment. As shown in FIG. 1, the X-ray computed tomography apparatus includes a gantry. The gantry rotatably supports an annular or disk-like rotating frame 2. An X-ray tube 3 and a two-dimensional detector system 4 are mounted on the rotating frame 2 so as to face each other through the object placed on the top in an imaging region. For the sake of descriptive convenience, the rotation axis of the rotating frame 2 is defined as the Z-axis, an imaging central axis connecting the focus of the X-ray tube 3 and the center of the two-dimensional detector system 4 is defined as the Y-axis, and an axis perpendicular to the X- and Z-axes is defined as the X-axis. At the time of imaging, the object P is typically placed in the imaging region such that the body axis almost coincides with the Z-axis. This X-Y-Z coordinate system forms a rotating coordinate system having the Z-axis as the rotation center.

The X-ray tube 3 generates X-rays upon receiving a high voltage and a filament current from a high voltage generation unit 5. If the two-dimensional detector system 4 is of a multislice type, it includes a plurality of detection element arrays, each including a plurality of channels in the channel direction (X-axis), in the slice direction (Z-axis). If the two-dimensional detector system 4 is of a two-dimensional array type, it includes a plurality of X-ray detection elements densely distributed in both the channel direction (X-axis) and the slice direction (Z-direction). The high voltage generation unit 5 applies a high voltage to the X-ray tube via a slip ring 1 in accordance with instruction information from a host controller.

A host controller 6 includes a CPU (Central Processing Unit) and a memory (neither of which is shown). The host controller 6 controls the operations of the high voltage generation unit 5, a gantry driving unit 7, and the like in accordance with instructions from an input device. Controlling the high voltage generation unit 5 will make the rotating frame 2 continuously rotate at a constant angular velocity and make the X-ray tube 3 generate X-rays continuously or at predetermined angular intervals. The gantry driving unit 7 can drive the top holding mechanism under the control of the host controller 6.

A data acquisition system 8 (DAS) is connected to the two-dimensional detector system 4. The data acquisition system 8 converts a current signal in each channel of the two-dimensional detector system 4 into a voltage, amplifies it, and converts it into a digital signal. The data (pure raw data) acquired by the data acquisition system 8 is transmitted to a preprocessing unit 10 via a noncontact type or slip ring type noncontact data transmission unit 9 using light or magnetism. The noncontact data transmission unit 9 sends the data (pure raw data) acquired by the data acquisition system 8 to the preprocessing unit 10. The preprocessing unit 10 performs preprocessing such as correction of sensitivity nonuniformity between channels for the pure raw data and correction of an extreme decrease in signal intensity or signal omission due to an X-ray absorber, mainly a metal portion with respect to the pure raw data.

A volume data reconstruction unit 11 generates a plurality of volume data files (time-series volume data files) at different imaging times based on data (projection data or raw data) corrected by the preprocessing unit 10. Although not shown, when a user such as a doctor or a technician operates an input unit 12 to input a command, the CPU executes a program stored in the memory. The input unit 12 is roughly constituted by a main console and a system console. A network communication unit 13 performs communication control corresponding to each protocol. The network communication unit 13 has a function of being able to be connected to a PACS (Picture Archiving and Communication Systems) or the like via an electric communication line such as a telephone line.

A lung field specifying unit 14 specifies lung field regions of an object by using volume data. There are various types of methods of specifying lung field regions of an object. They include a region expansion method and processing using a threshold (both of which will be described later). Lung field regions are air regions, which clearly differ in contrast from other organs. This makes it possible to relatively easily extract lung field regions by threshold processing.

A binary volume data generation unit 15 generates binary volume data by performing threshold processing for the volume data reconstructed by the volume data reconstruction unit 11. The binary volume data generation unit 15 generates a binary volume image by assigning a pixel value of 1 to low CT value regions in volume data and a pixel value of 0 to a region other than the low CT value regions.

A projection image generation unit 16 generates a projection image representing the distribution of low CT value regions and a projection image of the lung field regions by performing additive projection processing for binary volume data. Therefore, each coordinate value in a projection image is the sum of voxels each existing inside a projection line and having a pixel value of 1. A display unit 22 displays a projection image or the like under the control of the CPU.

A contour extraction unit 17 extracts the contours of the lung field regions for the projection image obtained by performing projection processing for the lung field region masks generated by the projection image generation unit. More specifically, the contour extraction unit 17 extracts the contours of the lung field regions by specifying pixels, out of all the pixels of the projection image, which have pixel values of 1 or more and are adjacent to pixels having a pixel value of 0.

A composite image generation unit 18 generates a composite image by superimposing the contours of the lung field regions extracted by the contour extraction unit 17 on the projection image obtained by projecting binary volume data. The composite image depicts the contour of the right lung field region, the contour of the left lung field region, and the left and right lung field regions representing the distributions of low CT value regions.

Figure 8:
FIG. 8 is a view showing a projection image of lung field region masks which are generated by the projection image generation unit in FIG. 1.

A graph generation unit 19 generates a graph three-dimensionally expressing a projection image based on a projection image (FIG. 8) representing a two-dimensional distribution concerning the thicknesses of low CT value regions (emphysema) standardized by equation (3) described later. The graph shown in FIG. 13 is an example of a polygonal graph obtained by connecting the centers of gravity of the upper surfaces of the respective three-dimensional bars in the histogram in FIG. 12 with lines. Stereoscopically expressing a projection image (FIG. 8) representing the two-dimensional distributions of pixel values standardized by equation (3) described later will express the magnitudes of low CT values as heights. It can therefore be expected to allow the user to grasp the distributions of low CT value regions more clearly than when grasping the distributions with color densities as shown in FIG. 8.

A storage unit 20 stores various data such as various volume data files (for example, generated volume data) and display images. An MPR image generation unit 21 generates an image representing an arbitrary slice of volume data.

Figure 3:
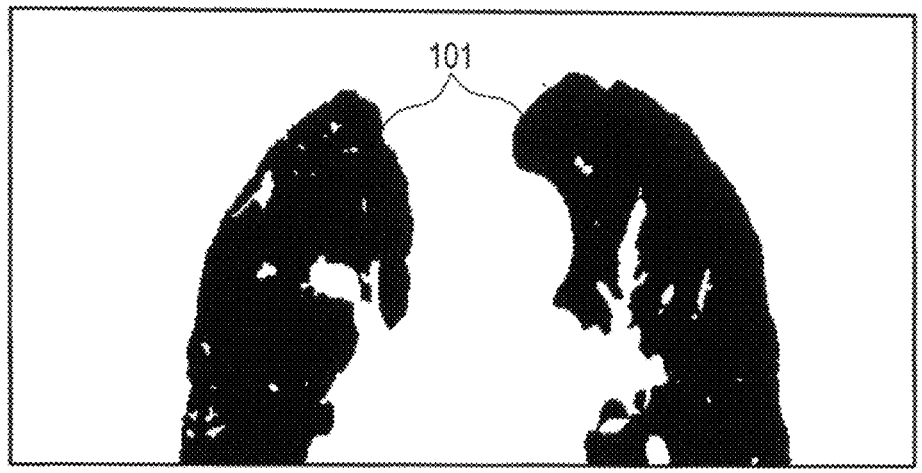
FIG. 3 is a view showing an image of the lung field regions (lung field region masks) extracted by a lung field region specifying unit in FIG. 1.

An image processing process according to this embodiment will be described below with reference to FIG. 2. First of all, the storage unit 20 inputs volume data of the chest region of the object in a memory or the like (step S11). The lung field specifying unit 14 then specifies lung field regions from the volume data by a method such as the region expansion method. The region expansion method is the processing of extracting regions in an input image by making the operator give pixels (seed points) as starting points designated in the lung field regions and sequentially integrating pixels adjacent to the designated pixels based on the similarities of density values. The lung field specifying unit 14 assigns a pixel value of 1 to lung field regions 101 and a pixel value of 0 to a region other than the lung field regions to generate lung field region masks as binary images, as shown in FIG. 3 (step S12).

Figure 4:
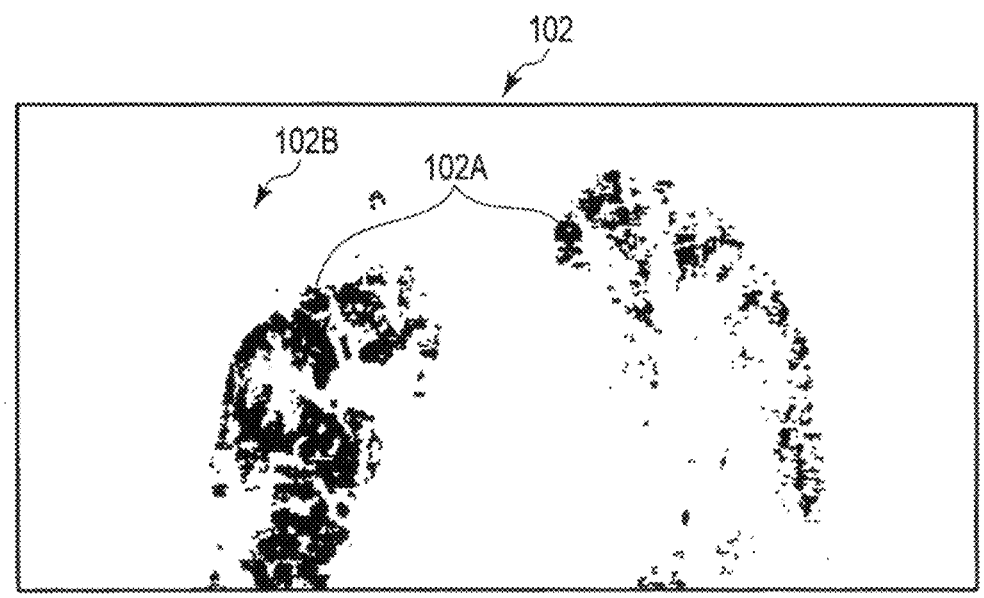
FIG. 4 is a view showing an example of the emphysema regions (emphysema region masks) extracted by a binary volume data generation unit in FIG. 1.

The binary volume data generation unit 15 then generates binary volume data in which low CT value regions (emphysema regions) are differentiated (or discriminated) from a region other than the low CT value regions by performing threshold processing using a CT value for volume data only within the lung field regions (step S13). More specifically, as shown in FIG. 4, the binary volume data generation unit 15 generates binary volume data (emphysema region masks) by assigning a pixel value of 1 to low CT value regions 102A in the lung field regions and assigning a pixel value of 0 to a region 102B other than the low CT value regions.

Figure 5:
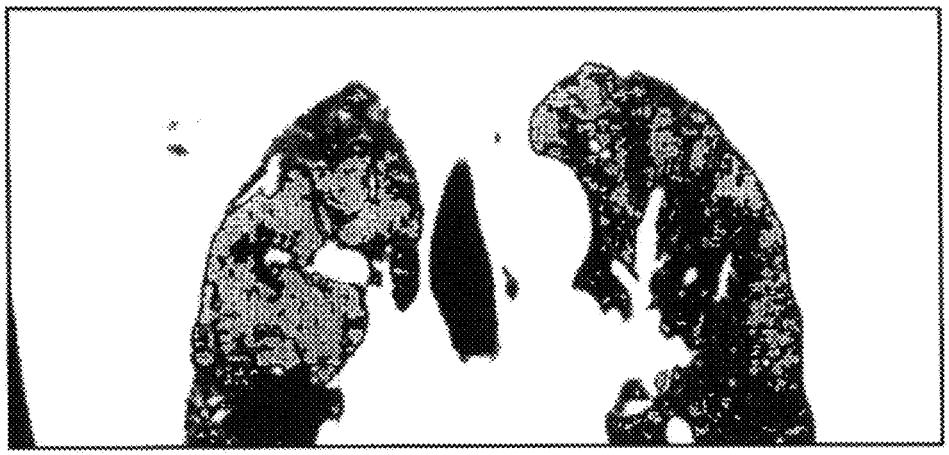
FIG. 5 is a view showing an image depicting a section obtained by cutting each colored emphysema region mask generated by the binary volume data generation unit in FIG. 1 in an arbitrary direction, with the section being superimposed on the MPR slice generated by an MPR image generation unit in FIG. 1.

FIG. 5 is a view showing a section obtained by cutting each colored emphysema region mask generated by the binary volume data generation unit 15 in FIG. 1 in an arbitrary direction, with the section being superimposed (additively projected) on an MPR slice. The MPR image is displayed in colors corresponding to pixel values in a color bar. Subsequently, the projection image generation unit 16 generates a projection image of the low CT value regions obtained by projecting three-dimensional low CT value region masks on a two-dimensional plane (step S14). A process of generating this projection image will be described in detail below.

First of all, the projection image generation unit 16 reads out the data of a generated low CT value region masks (emphysema region masks) from the storage unit 20. The projection image generation unit 16 performs, for example, coordinate conversion of the low CT value region masks so as to set the abscissa, the projection direction, and the body axis as the x-axis, the y-axis, and the z-axis, respectively, with the upper left of an axial plane being the origin. As indicated by equation (1) given below, in projection processing, the projection image generation unit 16 calculates the total sum of y-coordinates in the low CT value region mask with the x- and z-coordinates being fixed in defined (x, y, z) coordinates. This generates a projection image like that shown in FIG. 8.

$$\text{Map\_e}(x, z) = \sum_{i=1}^{512} \text{Mask\_e}(x, y_i, z) \tag{1}$$

where Mask_e(x, y, z) represents each pixel in the emphysema region mask (low CT value region mask). According to equation (1), there are 512 coronal slices. However, the number of coronal slices is not limited to 512 and can be an arbitrary integral value. When a calculation method like that indicated by equation (1) is to be used, there are available a method of generating a plurality of coronal slices concerning volume data and generating a projection image by using the coronal slices, and a method of generating a projection image by performing projection processing of each pixel in volume data without generating any coronal slices. In addition, slices to be used are not limited to coronal slices, and may be slices in arbitrary directions such as axial slices and sagittal slices.

Figure 12:
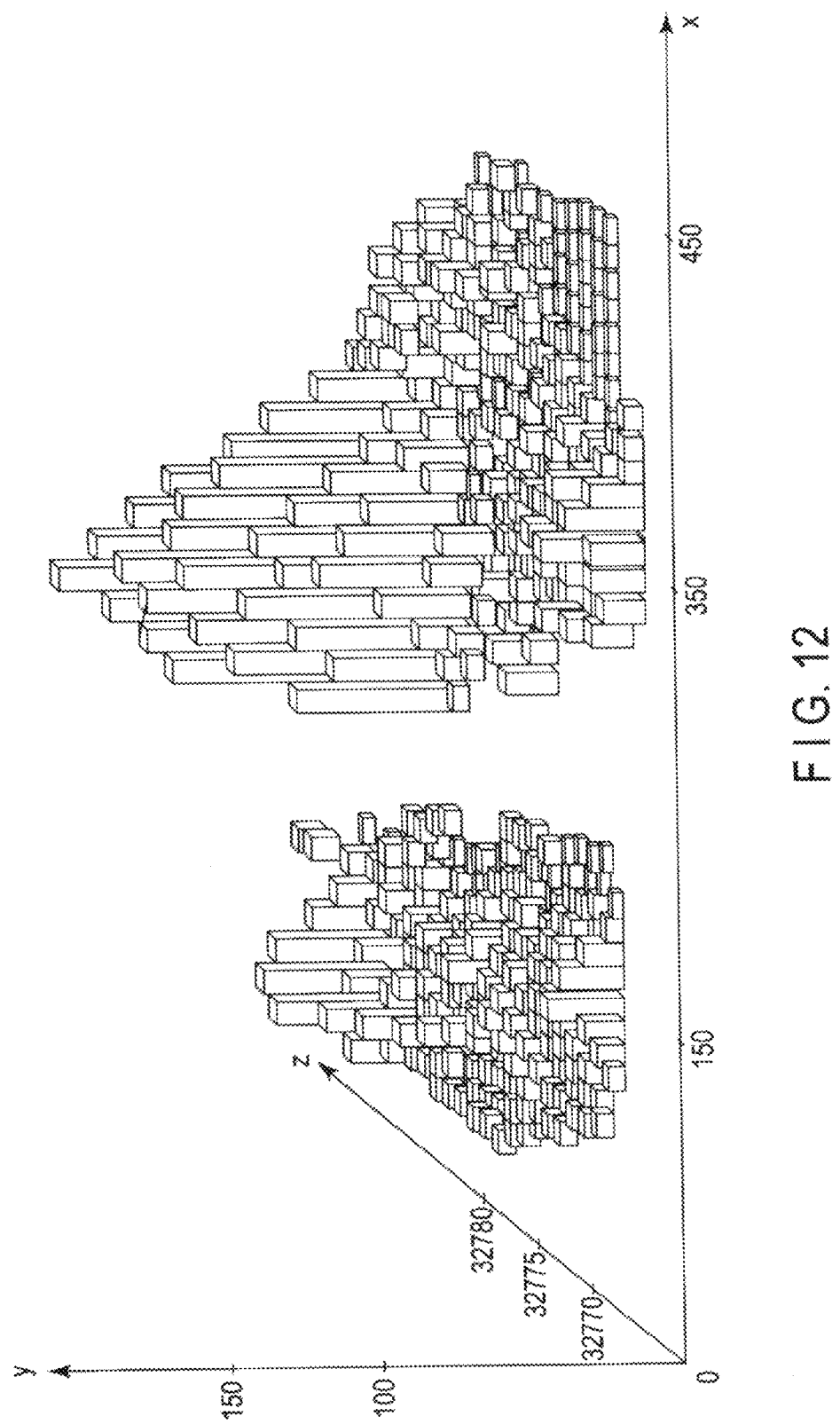
FIG. 12 is a view representing the projection image in FIG. 8 by a three-dimensional histogram.
Figure 13:
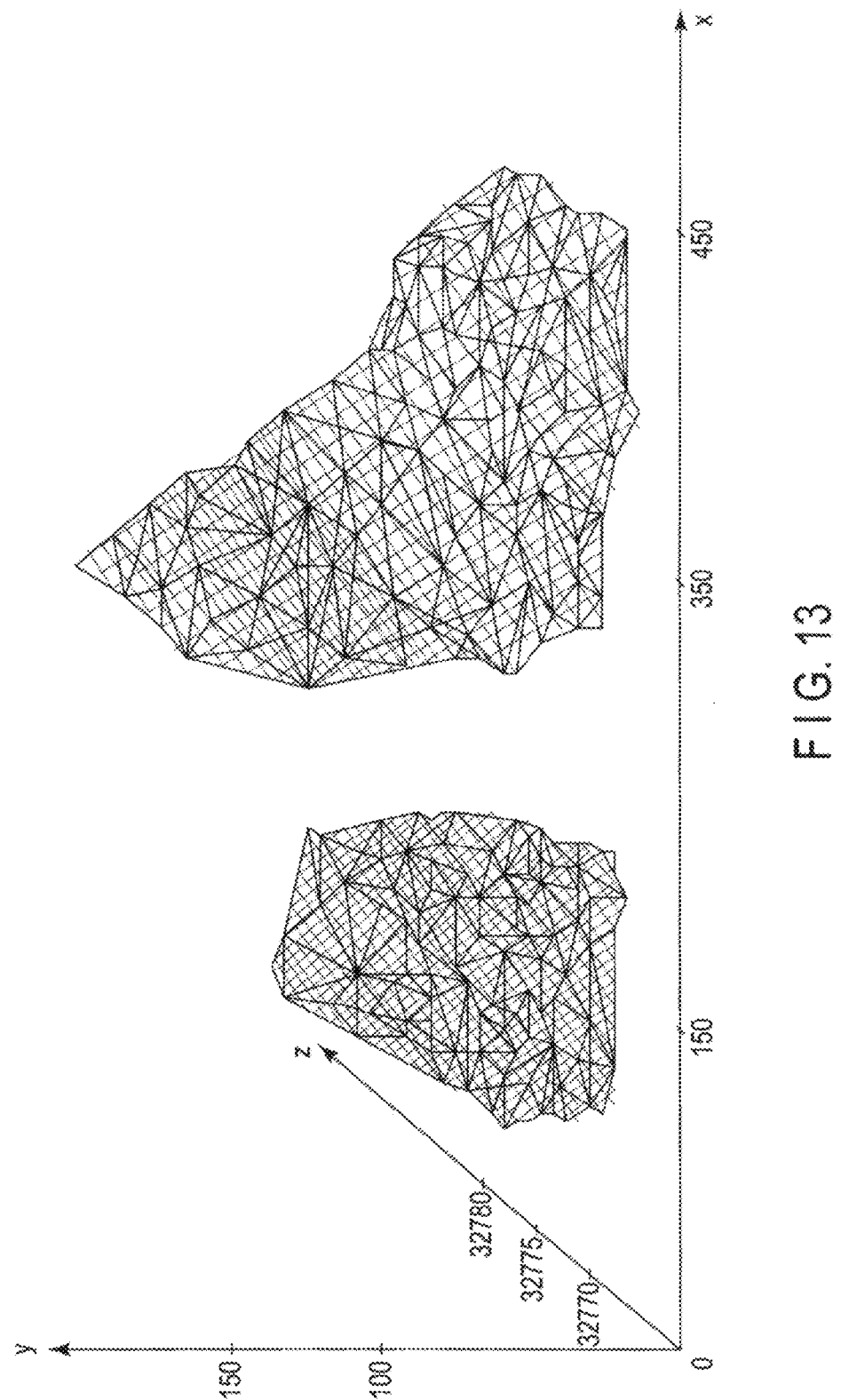
FIG. 13 is a view showing a three-dimensional plot generated from the three-dimensional histogram in FIG. 12.

FIG. 12 is a view schematically showing a procedure up to the generation of a projection image by projection processing using a plurality of coronal slices when using coronal slices. In this case, the coronal direction is decided as the imaging direction. First of all, the apparatus generates a plurality of coronal slices arranged along the coronal direction for the simplification of projection processing by using binary volume data (low CT value region mask). The apparatus then calculates Map_e(x, z) by adding the pixel values of all pixels along the y direction with respect to the respective coordinates of a plurality of coronal slices, with the x- and z-coordinates being fixed. When not using coronal slices, the apparatus calculates Map_e(x, z) by adding the pixel values of all pixels along the y direction with respect to the respective coordinates in binary volume data, with the x- and z-coordinates being fixed.

$$\text{Map\_l}(x, z) = \sum_{i=1}^{512} \text{Mask\_l}(x, y_i, z) \tag{2}$$

where Mask_l(x, y, z) represents each pixel in the lung field region mask. FIG. 8 shows an example of a projection image (Map_l(x, y, z)) of a generated lung field region mask. When performing the processing represented by equation (2), as in case of the processing represented by equation (1), there are available a method of generating a plurality of coronal slices along the coronal direction by using the lung field region masks and generating a projection image by using the coronal slices, and a method of generating a projection image by performing projection processing of each pixel in volume data without generating any coronal slices. When using coronal slices, the apparatus calculates Map_l(x, z) by adding the pixel values of pixels in all the coronal slices along the y direction with respect to the respective coordinates of the plurality of coronal slices, with the x- and z-axes being fixed. When not using coronal slices, the apparatus calculates Map_l(x, z) by adding the pixel values of all pixels along the y direction with respect to the respective coordinates in the lung field region mask, with the x- and z-coordinates being fixed.

Furthermore, the apparatus standardizes the thicknesses of low CT value regions along the projection axis with the thicknesses of the lung field regions by dividing Map_e(x, z) by Map_l(x, z) according to following equation. This allows to use the thicknesses of the regions as indices indicating the rates of development of emphysema in the lung field region. The absolute value of each coordinate in the projection plane obtained by projection processing as indicated by the left-hand side of equation (1) does not have much significance because different objects have different thicknesses, and hence is standardized in the above manner.

$$\text{Map\_}(x,z) = \text{Map\_}e(x,z)/\text{Map\_}l(x,z) \tag{3}$$

Figure 6:
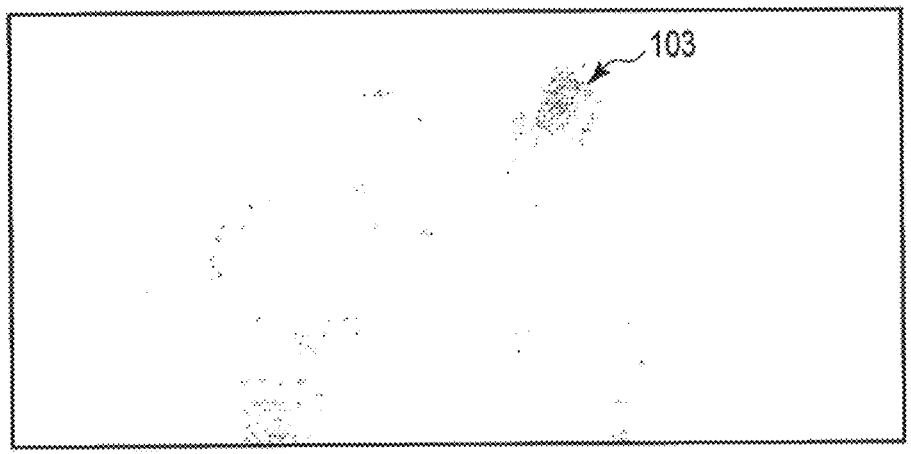
FIG. 6 is a view showing a projection image depicting the low CT value regions generated by a projection image generation unit in FIG. 1.

FIG. 6 shows an example of a projection image having the values represented by equation (3). In the projection image generated by the projection image generation unit and shown in FIG. 6, gray levels corresponding to the values represented by equation (3) are assigned to the pixel values in a low CT value region 103. Therefore, the projection image is expressed by a white/black pattern corresponding to the gray levels.

Figure 7:
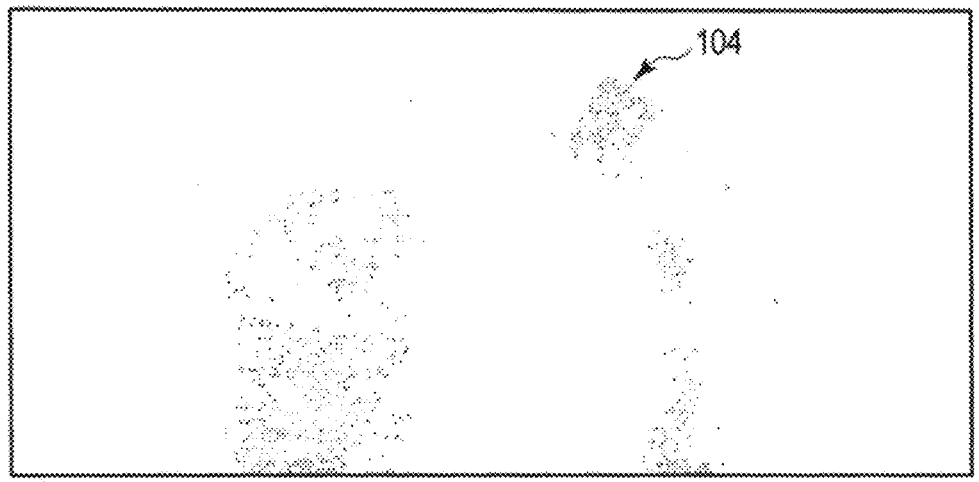
FIG. 7 is a view showing a projection distribution image obtained by converting the projection image in FIG. 6 into a color scale.

In addition, the projection image generation unit generates a colored projection image (FIG. 7) by coloring a projection image like that shown in FIG. 6. A low CT value region 104 is displayed in specific colors in a color bar associated with the values represented by equation (3). In parallel with step S14, the projection image generation unit generates a lung field region projection image by projecting three-dimensional lung field region masks having a pixel value of 1 on a two-dimensional plane only within the lung field regions (step S15). After the image processing in step S15, the apparatus extracts the contours of the lung field regions by making the contour extraction unit 17 extract pixels which are adjacent to pixels having a pixel value of 0 and have a pixel value of 1 or more by using the lung field projection image (step S16).

Figure 9:
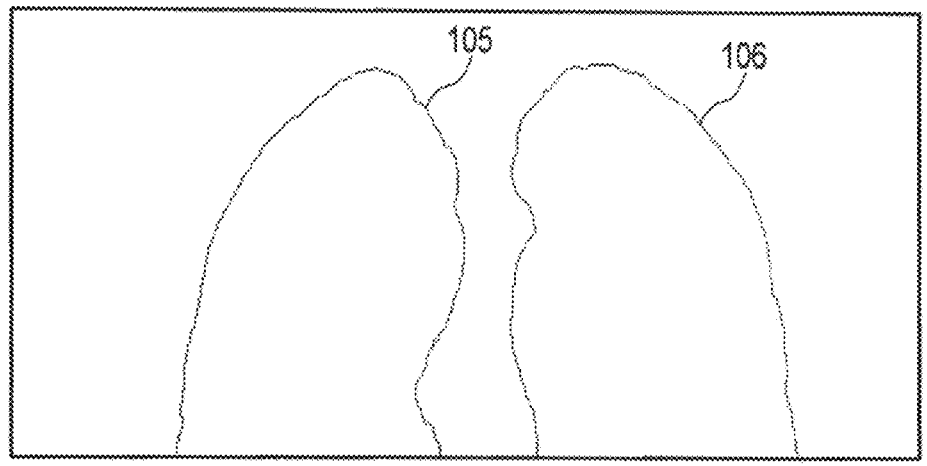
FIG. 9 is a view showing a contour image of the lung field regions extracted by a contour extraction unit.

FIG. 9 shows the contours of the specified lung field regions. As shown in FIG. 9, the image depicting the extracted contours of the lung field regions includes a contour 105 of the right lung field region and a contour 106 of the left lung field region.

Figure 10:
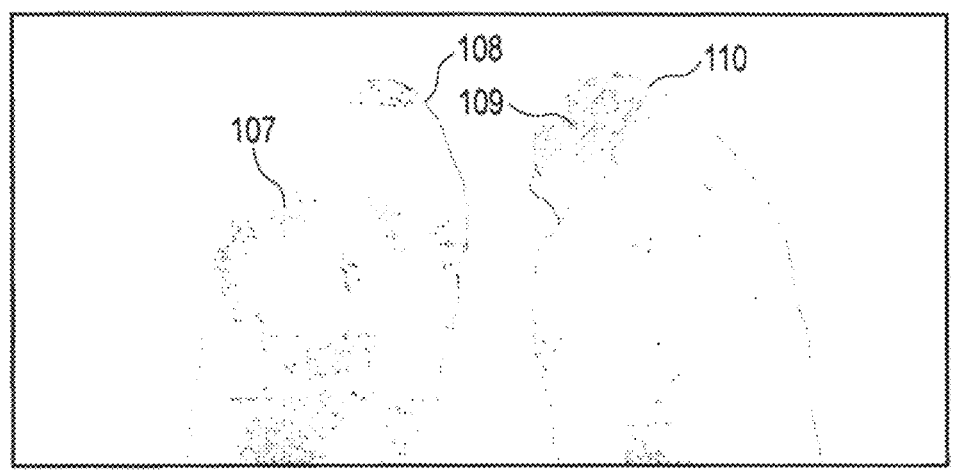
FIG. 10 is a view showing an image obtained by superimposing the contours in FIG. 9 on the projection distribution image in FIG. 7.

FIG. 10 shows the composite image obtained by superimposing extracted contours like those shown in FIG. 9 on the projection image shown in FIG. 8. A composite image is generated by the composite image generation unit 18. The composite image includes a right lung field region 107, a right lung field region 108, a left lung contour 109, and a left lung contour 110. Displaying a composite image obtained by combining contours with a projection image representing the distributions of low CT value regions allows to more clearly grasp the distributions of the positions of low CT value regions in lung field regions (step S17).

FIG. 11 is a schematic view showing a process from the generation of a plurality of coronal slices from binary volume data to the generation of a projection image by projection processing. The apparatus generates a plurality of coronal slices from binary volume data along the coronal direction. The apparatus generates a projection plane Map_e (x, z) by performing projection processing using pixel values Mask_e(x, $y_i$, z) respectively existing on 512 coronal slices with x and y being fixed.

FIG. 12 shows the projection image (FIG. 8) having the values calculated by equation (3), which is expressed by an expression form called a three-dimensional histogram. The numerals on the z-axis are values represented by equation (3). Stereoscopically displaying the values represented by equation (3) in this manner allows the user to clearly grasp the distributions of low CT value regions.

FIG. 13 is a graph representing a projection image having the values calculated by equation (3). In this graph, x', y', and z' given by an x'-y'-z' coordinate system respectively correspond to x, y, and Map(x, z). This generates a plot image like that shown in FIG. 13 by plotting corresponding points in a three-dimensional coordinate system (x', y', z') like that shown in FIG. 13 and connecting the plotted points with lines.

Note that the above embodiment has exemplified the case in which the presence of low CT value regions corresponding to the lung field regions is displayed by using coronal slices. However, this embodiment is not limited to this case and may display the presence of low CT value regions corresponding to the lung field regions by using axial slices or sagittal slices. For example, when using sagittal slices, the apparatus may segment the volume data acquired in step S13 into the first sub-volume including the left lung field region and the second sub-volume including the right lung field region and apply the processing in step S14 and the subsequent steps for each sub-volume by using sagittal slices as projection planes. Finally, the apparatus separately acquires the first image indicating the presence of a low CT value region corresponding to the left lung field region and the second image indicating the presence of a low CT value region corresponding to the right lung field region. Upon performing positional adjustment of the left and right lung field regions in step S17, the apparatus displays the first and second images as one image in a predetermined form.

An example of this embodiment has been described above. The followings are the effects expected from the embodiment. The user can grasp the distributions of low CT value regions (emphysema regions) in the entire lung field regions at a glance without checking all the slices of a CT image. In addition, it is therefore possible to save the labor of visually checking low CT value regions and reduce oversights. Furthermore, it is possible to reduce errors among users when determining low CT value region distributions.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus, comprising:
   an X-ray tube configured to generate X-rays;
   an X-ray detector configured to detect X-rays generated from the X-ray tube and transmitted through an object;
   processing circuitry configured to
      reconstruct first volume data of a chest region of the object based on an output from the X-ray detector;
      specify a lung field region of the object in the first volume data;
      generate second volume data in which a low CT value region is discriminated from a region other than the low CT value region in the lung field region; and
      generate an image representing a two-dimensional distribution of a ratio of values of the low CT value region to values of the lung field region based on the second volume data; and
   a display configured to display the generated image representing the two-dimensional distribution.

2. The X-ray computed tomography apparatus of claim 1, wherein the processing circuitry is further configured to generate images representing a plurality of two-dimensional distributions respectively corresponding to a plurality of times, and
   the display displays the plurality of two-dimensional distributions as a moving image.

3. The X-ray computed tomography apparatus of claim 1, wherein the processing circuitry is further configured to generate the second volume data in which the low CT value region is discriminated from the region other than the low CT value region, by performing threshold processing for the lung field region of the first volume data.

4. The X-ray computed tomography apparatus of claim 1, wherein the processing circuitry is further configured to generate a graph representing a two-dimensional distribution of the low CT value region by using the second volume data, and
   the display displays the graph.

5. The X-ray computed tomography apparatus of claim 4, wherein the processing circuitry is further configured to generate a plurality of slices with reference to a predetermined projection direction by using the second volume data and generate the graph based on the plurality of slices.

6. The X-ray computed tomography apparatus of claim 1, wherein the processing circuitry is further configured to generate the image representing the two-dimensional distribution of the ratio of the values of the low CT value region to the values of the lung field region by executing projection processing using a coronal slice as a projection plane.

7. The X-ray computed tomography apparatus of claim 1, wherein the processing circuitry is further configured to generate the image representing the two-dimensional distribution of the ratio of the values of the low CT value region to the values of the lung field region by executing projection processing using an axial slice as a projection plane.

8. The X-ray computed tomography apparatus of claim 1, wherein the processing circuitry is further configured to segment the second volume data into first sub-volume data including a left lung field region of the object and a second sub-volume data including a right lung field region of the object, and generate a first image representing a two-dimensional distribution of a ratio of the values of the low CT value region to values of the left lung field region and a second image representing a two-dimensional distribution of a ratio of the values of the low CT value region to values of the right lung field region, by executing projection processing for each of the first sub-volume data and the second sub-volume data.

9. The X-ray computed tomography apparatus of claim 8, wherein the display displays the first image and the second image such that a position of the left lung field region and a position of the right lung field region are associated with each other.

10. A medical image processing apparatus, comprising: processing circuitry configured to
reconstruct first volume data by using data obtained by X-ray CT scanning on a chest region of an object;
specify a lung field region of the object in the first volume data;
generate second volume data in which a low CT value region is discriminated from a region other than the low CT value region in the lung field region; and
generate an image representing a two-dimensional distribution of a ratio of values of the low CT value region to values of the lung field region based on the second volume data; and
a display configured to display the generated image representing the two-dimensional distribution.

11. The medical image processing apparatus of claim 10, wherein the processing circuitry is further configured to generate images representing a plurality of two-dimensional distributions respectively corresponding to a plurality of times, and
the display displays the plurality of two-dimensional distributions as a moving image.

12. The medical image processing apparatus of claim 10, wherein the processing circuitry is further configured to generate the second volume data in which the low CT value region is discriminated from the region other than the low CT value region, by performing threshold processing for the lung field region of the first volume data.

13. The medical image processing apparatus of claim 10, wherein the processing circuitry is further configured to generate a graph representing a two-dimensional distribution of the low CT value region by using the second volume data, and
the display displays the graph.

14. The medical image processing apparatus of claim 13, wherein the processing circuitry is further configured to generate a plurality of slices with reference to a predetermined projection direction by using the second volume data and generate the graph based on the plurality of slices.

15. The medical image processing apparatus of claim 10, wherein the processing circuitry is further configured to generate the image representing the two-dimensional distribution of the ratio of the values of the low CT value region to the values of the lung field region by executing projection processing using a coronal slice as a projection plane.

16. The medical image processing apparatus of claim 10, wherein the processing circuitry is further configured to generate the image representing the two-dimensional distribution of the ratio of the values of the low CT value region to the values of the lung field region by executing projection processing using an axial slice as a projection plane.

17. The medical image processing apparatus of claim 10, wherein the processing circuitry is further configured to
segment the second volume data into first sub-volume data including a left lung field region of the object and a second sub-volume data including a right lung field region of the object, and
generate a first image representing a two-dimensional distribution of a ratio of the values of the low CT value region to values of the left lung field region and a second image representing a two-dimensional distribution of a ratio of the values of the low CT value region to values of the right lung field region, by executing projection processing for each of the first sub-volume data and the second sub-volume data.

18. The medical image processing apparatus of claim 17, wherein the display displays the first image and the second image such that a position of the left lung field region and a position of the right lung field region correspond to each other.

19. A medical image processing method comprising:
specifying a lung field region of an object in first volume data reconstructed by using data obtained by X-ray CT scanning on a chest region of the object;
generating second volume data in which a low CT value region is discriminated from a region other than the low CT value region in the lung field region;
generating an image representing a two-dimensional distribution of a ratio of values of the low CT value region to values of the lung field region based on the second volume data; and
displaying the generated image representing the two-dimensional distribution.

* * * * *